(12) United States Patent
Orban, III

(10) Patent No.: US 6,971,988 B2
(45) Date of Patent: Dec. 6, 2005

(54) ENDOSCOPIC TISSUE REMOVAL APPARATUS AND METHOD

(75) Inventor: Joseph P. Orban, III, Norwalk, CT (US)

(73) Assignee: Tyco Healthcare Group, LP, Norwalk, CT (US)

( * ) Notice: Subject to any disclaimer, the term of this patent is extended or adjusted under 35 U.S.C. 154(b) by 0 days.

(21) Appl. No.: 10/801,441

(22) Filed: Mar. 16, 2004

(65) Prior Publication Data

US 2004/0242960 A1    Dec. 2, 2004

Related U.S. Application Data

(60) Provisional application No. 60/455,261, filed on Mar. 17, 2003.

(51) Int. Cl.$^7$ ............................................... A61B 1/00
(52) U.S. Cl. ...................... 600/104; 600/106; 600/153; 600/562
(58) Field of Search ................ 600/101, 104, 600/106, 153, 562; 606/106, 107, 113, 114, 606/205

(56) References Cited

U.S. PATENT DOCUMENTS

| | | | |
|---|---|---|---|
| 4,611,594 A | 9/1986 | Grayhack et al. | |
| 5,176,687 A | 1/1993 | Hasson et al. | |
| 5,190,561 A * | 3/1993 | Graber | 606/127 |
| 5,215,521 A | 6/1993 | Cochran et al. | |
| 5,312,417 A | 5/1994 | Wilk | |
| 5,337,754 A | 8/1994 | Heaven et al. | |
| 5,370,647 A | 12/1994 | Graber et al. | |
| 5,486,183 A | 1/1996 | Middleman et al. | |
| 5,643,282 A | 7/1997 | Kieturakis | |
| 5,667,480 A | 9/1997 | Knight et al. | |
| 5,722,934 A | 3/1998 | Knight et al. | |
| 5,725,479 A | 3/1998 | Knight et al. | |
| 5,782,747 A * | 7/1998 | Zimmon | 600/104 |
| 5,853,374 A | 12/1998 | Hart et al. | |
| 5,902,315 A | 5/1999 | DuBois | |
| 5,908,435 A | 6/1999 | Samuels | |
| 5,924,175 A | 7/1999 | Lippitt et al. | |
| 5,928,135 A | 7/1999 | Knight et al. | |
| 5,928,138 A | 7/1999 | Knight et al. | |
| 5,980,544 A | 11/1999 | Vaitekunas | |
| 5,989,274 A | 11/1999 | Davison et al. | |
| 6,162,235 A | 12/2000 | Vaitekunas | |
| 6,193,653 B1 | 2/2001 | Evans et al. | |
| 6,270,505 B1 | 8/2001 | Yoshida et al. | |
| 6,383,195 B1 | 5/2002 | Richard | |
| 6,387,109 B1 | 5/2002 | Davison et al. | |
| 6,471,709 B1 * | 10/2002 | Fawzi et al. | 606/114 |
| 6,589,252 B2 * | 7/2003 | McGuckin, Jr. | 606/114 |
| 6,656,176 B2 | 12/2003 | Hess et al. | |
| 2003/0120281 A1 * | 6/2003 | Bates et al. | 606/114 |

* cited by examiner

*Primary Examiner*—Beverly M. Flanagan

(57) ABSTRACT

An apparatus for withdrawing a tissue specimen being held by a grasping instrument through an endoscope includes an endoscope having an endoscopic shaft with proximal and distal ends and a lumen extending therebetween. The apparatus also includes first and second hoop-like support members which are selectively slideable within the lumen from a first position to at least one second position. Each of the hoop members includes a diameter which is variable from a first diameter to at least one different diameter. The apparatus also includes a pouch having first and second ends which attach to respective first and second hoop members. The pouch defines a container therein for retaining the tissue specimen. A pair of drawstrings are attached to the first and second ends of the pouch, respectively, and are remotely operable to close the ends about the tissue specimen.

9 Claims, 2 Drawing Sheets

ENDOSCOPIC TISSUE REMOVAL APPARATUS AND METHOD

CROSS REFERENCE TO RELATED APPLICATION

This application claims the benefit of priority to U.S. Provisional Application Ser. No. 60/455,261 filed on Mar. 17, 2003 by Joseph P. Orban, III entitled "ENDOSCOPIC TISSUE REMOVAL APPARATUS AND METHOD" the entire contents of which is hereby incorporated by reference herein.

BACKGROUND

1. Field of the Invention

The present disclosure relates to an endoscopic tissue retrieval apparatus and method for utilizing the same. More particularly, the present disclosure relates to a remotely-operated tissue retrieval apparatus which utilizes an expandable pouch or bag to retrieve tissue through an endoscope during minimally invasive surgical procedures.

2. Background of the Art

Over the past several decades, modern medicine has witnessed tremendous advances in less invasive and less traumatic surgical procedures which has provided numerous physical and economical benefits to the modern patient. For example, more and more surgeons are abandoning traditional open methods of gaining access to vital organs and body cavities in favor of endoscopes and endoscopic instruments which access organs through small puncture-like incisions.

Laparoscopic and endoscopic surgical procedures are minimally invasive procedures in which operations are carried out within the body by means of elongated instruments inserted through these small incisions in the body. The opening is typically created by a tissue piercing instrument such as a trocar. Endoscopic instruments are inserted into the patient through a cannula or port which maintains the incision opening in the body during the procedure. A lumen is typically defined through the endoscope and enables the surgeon to selectively introduce various endoscopic instrumentation into the operating cavity as needed.

Because the interior dimension of the lumen is relatively narrow only small instruments can be inserted therethrough which limits certain surgeries. However, new endoscopic designs and procedures are enabling more and more complex and intricate surgeries to be performed through these minimal access incisions. For example, a surgeon can remotely introduce these small sophisticated endoscopic instruments into the surgical cavity and excise or resect relatively large volumes of tissue, tumors, organs and the like from outside the surgical cavity as needed during a particular surgical procedure, e.g., nephrectomy, cholecystectomy. Unfortunately, the extraction and removal of such excised tissues, tumors, organs or the like has proven to be somewhat complicated due to the relative size of the excised tissue, tumors, organs compared to the interior dimensions of the endoscope lumen. In addition, the removal of certain malignant (non-benign) tissue, i.e., infected/contaminated tissue, cancerous tumors, etc., tends to be even more complicated due to the need to contain the malignant tissue during removal to prevent further infection.

Several prior art devices have been developed to facilitate removal of the tissue specimen after resection. For the most part, these devices relate to entrapment-like devices in which the tissue specimen is dropped into a specimen bag which is then withdrawn through the incision. For example, U.S. Pat. No. 5,465,731 and U.S. Pat. No. 5,647,372 both relate to a specimen removal pouch made from a flexible membrane which includes a drawstring disposed circumferentially round the end of the pouch. Once a piece of tissue is resected, the specimen is dropped into a pouch and the drawstring is pulled which closes the mouth of the pouch about the specimen. The neck of the pouch is then positioned against the distal end of the cannula and the whole assembly is subsequently removed. The entire disclosure of both of these applications is hereby incorporated by reference herein.

Although entrapment bags are useful, there remains a need for an improved specimen retrieval apparatus which facilitates endoscopic tissue containment and removal in minimally invasive surgical procedures.

SUMMARY

The present disclosure relates to an apparatus for withdrawing a tissue specimen and includes an endoscope having an endoscopic shaft with proximal and distal ends and a lumen extending therebetween. The tissue withdrawing apparatus also includes at least one hoop-like support member which is selectively slideable within the lumen from a first position wherein the hoop like member has a first diameter to at least one second position wherein the hoop-like member has a second diameter which is different from the first diameter. A pouch is also included which has first and second ends. The first end of the pouch is an open end which is attached to the at least one hoop-like support member. The pouch defines a container therein for retaining the tissue specimen. A remote actuator is also included and is disposed proximate the proximal end of the endoscopic shaft. The remote actuator is selectively actuateable to close the first end to encapsulate the tissue specimen.

In one embodiment according to the present disclosure a second hoop-like support member is included and the second end of the pouch is an open end attached to the second hoop-like support member. In another embodiment, the pouch includes at least one strut disposed between the hoop-like support members for further defining the container for retaining the tissue specimen.

Preferably, the diameter of the second hoop-like support member is selectively expandable from a first diameter within the lumen to a second diameter outside the lumen. In yet another embodiment according to the present disclosure, the diameter of the first hoop-like support member is selectively contractible from a first diameter within the lumen to a second diameter within the lumen.

The present disclosure also relates to an apparatus for withdrawing a tissue specimen through an endoscope wherein the endoscope includes a shaft with proximal and distal ends and a lumen extending therebetween. The apparatus of the present disclosure also includes first and second hoop-like support members, which are selectively slideable/translatable within the lumen from a first position to at least one second position. Each of the hoop members includes a diameter which is variable from a first diameter to at least one different diameter. A pouch is included which has first and second ends which attach to respective first and second hoop members. The interior of the pouch defines a container for retaining the tissue specimen. A pair of drawstrings are attached to the first and second ends of the pouch, respectively, and are remotely operable to close the ends about the tissue specimen. Preferably, the pouch includes at least one strut disposed between the hoop members for further defining the container for retaining the tissue specimen.

In one embodiment according to the present disclosure, the diameter of the second hoop member is selectively expandable from a first diameter within the lumen to a second diameter outside the lumen. Preferably, the second hoop member is disposed in a pre-loaded configuration within the lumen such that the diameter of the second hoop member automatically expands when the second hoop member is extended from the distal end of the endoscopic shaft. In another embodiment, the diameter of the first hoop member is selectively contractible from a first diameter within the lumen to a second diameter within the lumen. In yet still another embodiment, the hoop members include a pair of arcuate portions which slidingly reciprocate one another to vary the diameter of each respective hoop member.

The present disclosure also relates to a method for withdrawing a tissue specimen through an endoscope and includes the steps of providing: a grasping instrument; an endoscope including an endoscopic shaft having proximal and distal ends and a lumen extending therebetween; first and second hoop-like support members, each of the hoop members being selectively slideable within the lumen from a first position to at least one second position, each of the hoop members including a diameter which is variable from a first diameter to at least one different diameter; and a pouch having first and second ends which attach to respective first and second hoop members, the pouch defining a container therein for retaining the tissue specimen.

The method further includes the steps of: grasping the tissue specimen with the grasping instrument; sliding the first and second hoop-like members from the first to second position such that the diameter of the second hoop-like member expands and encapsulates the tissue specimen; closing the second end of the pouch about the tissue specimen; withdrawing the grasping instrument through the lumen; closing the first end of the pouch about the tissue specimen; and withdrawing the tissue specimen and pouch proximally through the lumen.

BRIEF DESCRIPTION OF THE DRAWINGS

Embodiments of the presently disclosed endoscopic tissue removal apparatus and method are described herein with reference to the drawings, wherein.

DETAILED DESCRIPTION

Figure 1A:
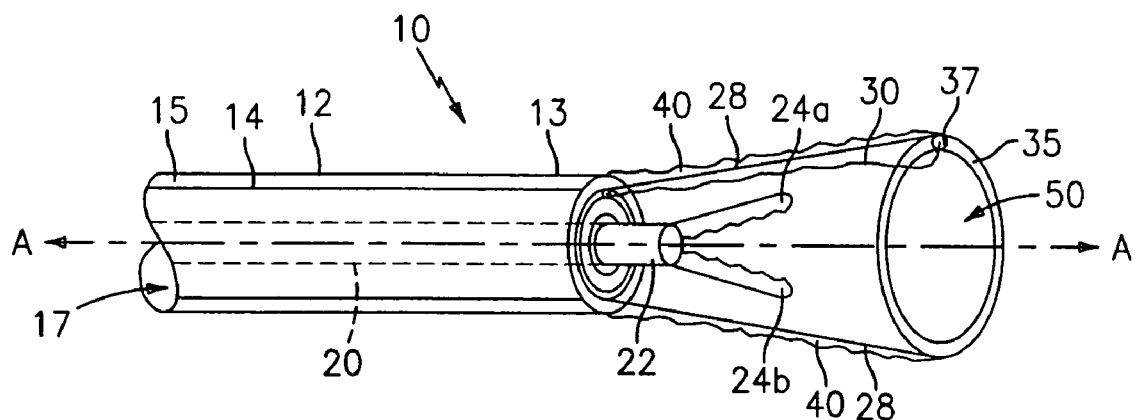
FIG. 1A is a schematically-illustrated, side view showing an endoscopic tissue removal apparatus in accordance with the present disclosure shown in deployed orientation with a grasping instrument disposed within a specimen retrieval pouch.

Referring now in specific detail to the drawings in which like reference numerals identify similar or identical elements throughout the several views, one embodiment of an endoscopic tissue retrieval apparatus is shown in FIGS. 1A–2E and is generally identified as retrieval apparatus 10.

The endoscopic retrieval apparatus 10 includes an endoscopic shaft 12 having proximal and distal ends 15 and 13, respectively, and a lumen 17 which extends therethrough between the proximal 15 and distal ends 13. The lumen 17 is internally dimensioned to reciprocate an endoscopic grasper or forceps 20 along a longitudinal axis "A" defined therethrough as explained in more detail below with respect to the operation of the tissue retrieval apparatus 10. As can be appreciated, the lumen 17 may also be dimensioned to allow selective reciprocation of other surgical instruments therethrough which may be utilized during a typical tissue removal procedure, e.g., a resector, a biopsy instrument, an electrosurgical pencil, or the like. As will be explained in more detail below, one or more of these instruments may be utilized to cut the tissue specimen 100 from the body for subsequent grasping and removal from the operating cavity.

The retrieval apparatus 10 also includes a retrieval pouch or bag 40 which is disposed within the lumen 17. The pouch 40 is preferably made from a flexible membrane or other bio-compatible material. Pouch 40 includes a pair of hoop-like support members 35 and 65 located at the distal and proximal ends thereof. As explained in more detail below with respect to the operation of the tissue retrieval apparatus 10, the pouch 40 is initially positioned within the lumen 17 in a manner suitable for deployment from a distal end 13 of the endoscopic shaft 12. More particularly, at least the distal hoop member 35 is selectively expandable from a first, pre-deployed orientation inside the lumen 17 to a second, deployed configuration when positioned outside the lumen 17. Both hoop members 35 and 65 are selectively collapsible to contain the tissue specimen 100 which is explained in more detail below with respect to the operation of the instrument below. As can be appreciated, the configuration of hoop members 35 and 65 does not impede longitudinal reciprocation of the grasping instrument 20 (or, other type of endoscopic instrument) within the lumen 17 to grasp or otherwise manipulate the tissue specimen 100. It is also envisioned that either a proximal hoop member 65 or distal hoop member 35 may be used so that the retrieval apparatus has only one hoop.

Figure 2A:
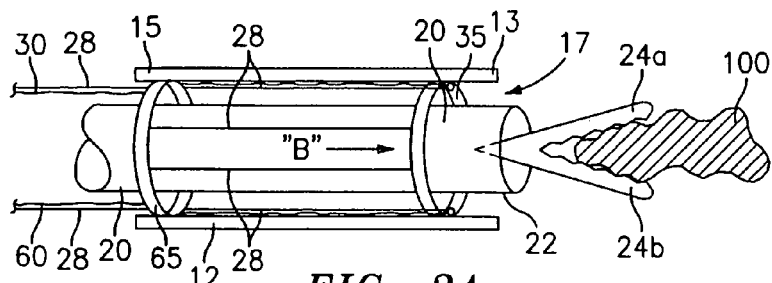
FIGS. 2A–2E are schematically-illustrated views of the tissue removal apparatus of FIG. 1 grasping, containing and removing a tissue specimen through a lumen disposed within an endoscopic instrument.
Figure 2B:
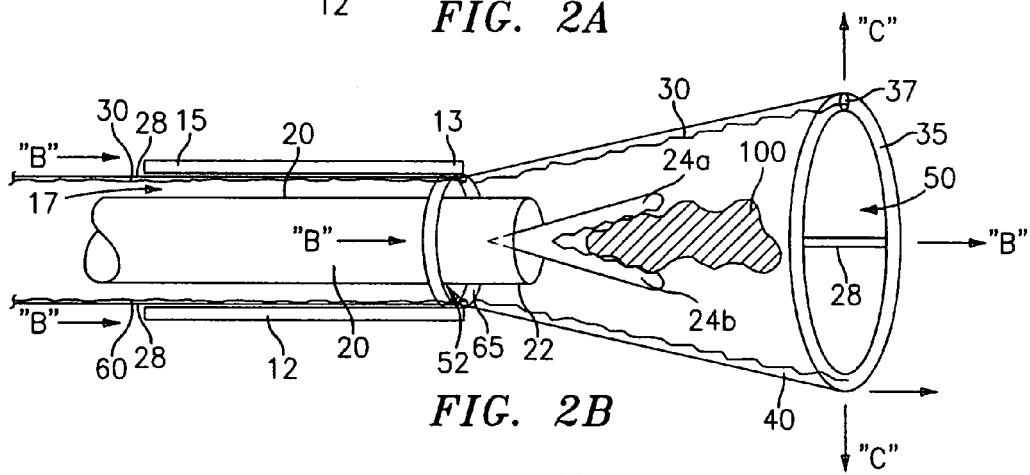

A series of support structures or struts 28 are disposed between the proximal and distal hoop members 65 and 35 to further define the pouch 40 and to facilitate deployment and positioning of the pouch 40 from the distal end 13 of the endoscopic shaft 12. As best illustrated in FIG. 2B, the support struts 28 and the hoop members 35 and 65 form a generally conical structure having its apex defining a first opening 52 in the proximal end 39 of the pouch 40 and a second opening 50 at the distal end 41 of the pouch 40. The dimensions of each of the openings 50 and 52 are generally defined by the dimensions of the hoop members 35 and 65, respectively.

The support struts 28 are configured to extend proximally through the lumen to allow a user to remotely deploy the specimen retrieval pouch 40 from the shaft 12 to collect and encapsulate a specimen 100 as needed during the procedure (See, e.g., FIGS. 2A–2E). It is also envisioned that the pouch 40 could be formed from material having suitable structural integrity to maintain the pouch 40 in a deployed configuration without the need for the support struts 28. As can be appreciated, in this embodiment the pouch 40 would include a mechanical interface (not shown) which attaches to the pouch 40 to permit remote deployment of the pouch 40 from the shaft 12. Preferably, the struts 28 are integrated with the overall structure of the pouch 40 and are made from materials having the requisite strength and flexibility to support the pouch 40 during deployment and encapsulation of the tissue sample 100.

As best illustrated in FIGS. 2A–2E, the distal hoop member 35 is configured to be selectively expandable between a first diameter inside the lumen 17 of shaft 12 to a second, expanded diameter when positioned outside shaft 12. More particularly, when disposed in the first configuration, hoop member 35 is biased or pre-loaded such that, once released from the distal end 13 of shaft 12, the hoop member 35 automatically expands to the second, larger diameter. As can be appreciated, the larger diameter of second opening 50 facilitates encapsulation of the tissue sample 100 within pouch 40. The struts 28 maintain the sides of the pouch 40 in an open configuration between the hoop members 35 and 65 which facilitates encapsulation of the tissue specimen 100.

Figure 1B:
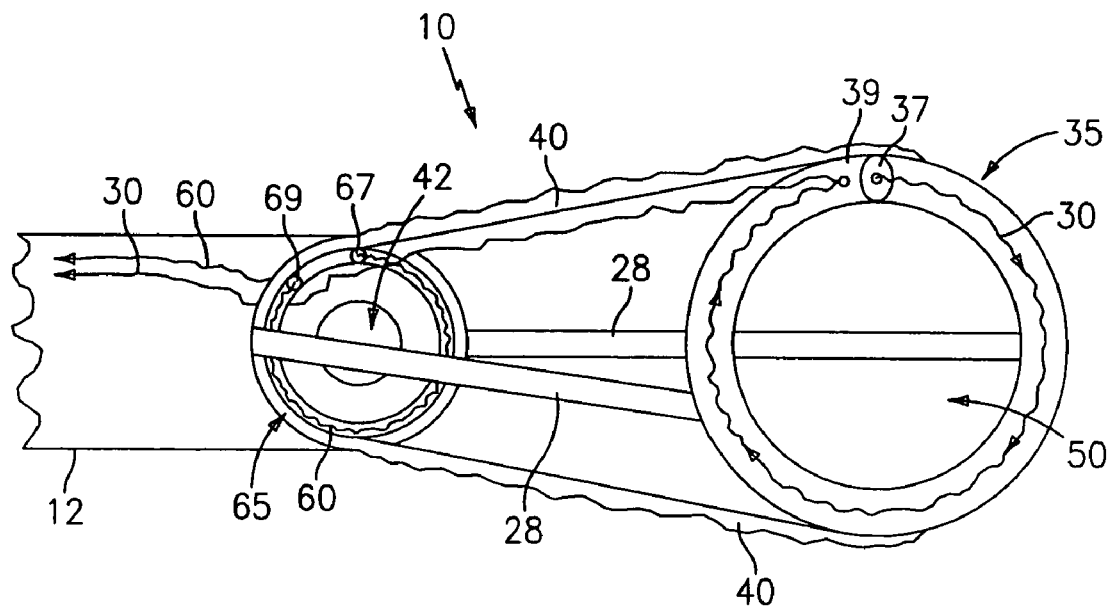
FIG. 1B is an enlarged schematic view of the tissue removal apparatus of FIG. 1 showing a pair of drawstrings which are remotely operable to selectively close the distal and proximal ends of the specimen pouch.

Preferably, the distal hoop member 35 is configured to include a pair of telescoping or inter-engaging arcuate portions 37 and 39 which slidingly reciprocate one another to permit expansion and contraction of the hoop member 35 as needed. More particularly and as mentioned above, prior to deployment, hoop member 35 is held in a pre-loaded orientation within lumen 17. Once deployed, i.e., hoop member 35 is forced via support strut 28 from the distal end 13 of shaft 12, the distal ends of the arcuate portions 37 and 39 move away from one another (i.e., biased outwardly) to allow for hoop member 35 to freely expand to the second, larger diameter to encapsulate the tissue specimen 100 (See. FIGS. 1B and 2B).

After the tissue specimen 100 is encapsulated, a drawstring or suture 30 (or the like) is pulled to contract the hoop member 35 and contain the tissue specimen 100 as explained in more detail below. As can be appreciated, the hoop member 35 may be contracted beyond the hoop member's 35 original, preloaded configuration within the lumen which further closes the distal opening 50 of the pouch 40 to securely retain the tissue specimen 100 thereinside (See FIGS. 2C–2E). For example, hoop member 35 is desirably biased toward the expanded configuration. The drawstring 30 preferably has suitable strength to overcome the bias of the struts 28 and the hoop member 35 to close the distal opening 50 of the pouch 40 for withdrawal.

Likewise, the proximal opening 52 is also desirably configured for selective closure. More particularly, the proximal hoop member 65 also includes arcuately-shaped telescopic members 67 and 69 which slidingly reciprocate one another to permit a user to remotely contract the proximal hoop member 65 via suture 60 (or the like) as needed after the tissue specimen 100 is collected. It is envisioned that the hoop members 35 and 65 may be selectively expanded and contracted in other mechanical or electromechanical manners, e.g., iris valves, shape memory alloys, balloons, piezoelectric alloys, etc. It is also contemplated, that proximal hoop member 65 may be configured in a pre-loaded configuration such that the arcuate members 67 and 69 of the hoop member 65 automatically contract once activated either mechanically or electro-mechanically. The hoop members may be biased toward the expanded or contracted configuration.

It is envisioned that one or both hoop members, e.g., proximal hoop member 65 and the pouch 40 are removably connected to the distal end 13 of the shaft 12 such that, upon contraction, the hoop member 65 or the pouch 40 disengages from the distal end 13 of the shaft 12 to close opening 52 about the tissue specimen 100. As can be appreciated, this facilitates withdrawal of the tissue specimen 100 through the lumen 17.

In use and as best illustrated in FIGS. 2A–2E, the endoscopic shaft 12 is inserted through a cannula (not shown) and into the operating cavity. A biopsy instrument, a resection instrument, scissors, or the like is inserted through the lumen 17 to separate the tissue specimen 100 from the surrounding tissue such as in a biopsy, nephrectomy, cholecystectomy, etc. Once the tissue specimen has been resected, the endoscopic forceps 20 is inserted through the lumen 17 to manipulate and grasp the tissue specimen 100.

The forceps 20 includes jaw members 24a and 24b which are selectively movable relative to one another from a first approximation position to a second closed position to grasp tissue 100 therebetween. This enables the surgeon to position the tissue for encapsulation. It is envisioned that numerous types of endoscopic forceps may be utilized to grasp and retain the tissue specimen 100. Moreover, it is also contemplated that a combination instrument may be utilized to both resect and retain the tissue specimen 100 for withdrawal. Preferably, the forceps 20 is selectively translatable along and rotatable about longitudinal axis "A" to facilitate manipulating of the tissue specimen 100 (See FIG. 1A). It is also contemplated that the forceps 20 may include an articulation feature which rotates the jaw members 24a and 24b relative to longitudinal axis "A" to further facilitate manipulation and positioning of the tissue specimen 100.

Once the specimen 100 is grasped, the operator remotely actuates the support struts 28 to deploy the specimen pouch 40. More particularly, the struts 28 are pushed distally in the direction "B" to force hoop member 35 from the distal end 35 of the shaft 12. As best shown in FIG. 2B, once the hoop member 35 extends beyond distal end 13, the pre-loaded or arcuate portions 35 and 37 deploy (i.e., freely move away from one another) and expand the diameter of the second opening 50 in the direction "C". The proximal hoop member 65 remains within lumen 17 of shaft 12. As a result thereof, the pouch 40 expands into a generally conical configuration and encapsulates, i.e., captures, the tissue specimen 100.

Figure 2C:
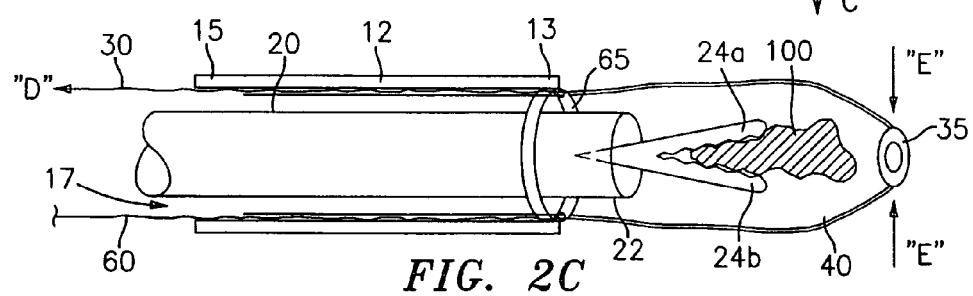

Once the pouch 40 has been deployed about the tissue specimen 100, the user pulls the first drawstring 30 in the proximal direction which cinches and closes the distal opening 50 in the direction "E" to contain the specimen 100. More particularly, pulling the drawstring 30 in the direction "D" telescopically reciprocates arcuate portion 39 within arcuate portion 37 (or vice versa) which reduces the diameter of the opening 50 as best illustrated in FIG. 2C.

Figure 2D:
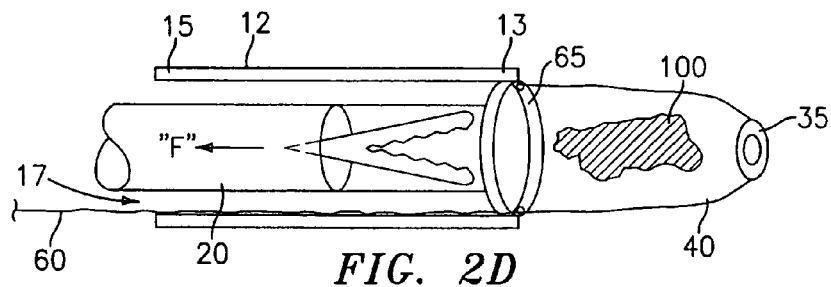

After the distal opening 50 has been closed, the user actuates the grasping instrument 20 to release the tissue specimen 100 and thereafter withdraws the grasping instrument 20 from the operating site in the direction "F" through lumen 17 (See FIG. 2D). Once the grasping instrument 20 has been withdrawn, the user pulls the second drawstring 60 in the proximal direction "G" which closes the proximal opening 42 in the direction "H" to contain the tissue specimen 100 (See FIG. 2E). The tissue specimen pouch 40 is then withdrawn from the operating site through lumen 17. Preferably, drawstring 60 may also be utilized to withdraw specimen 100 through lumen 17.

Figure 2E:
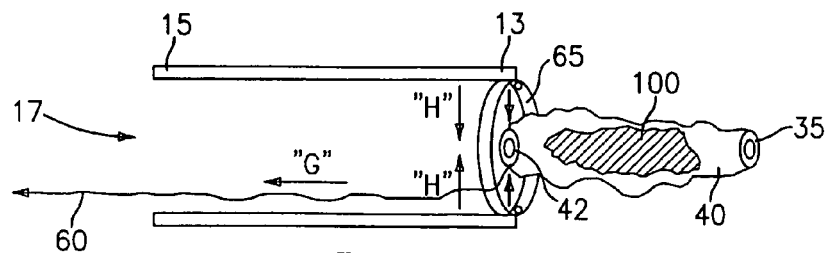

It is contemplated that the proximal end 42 of pouch 40 may be configured such that pulling drawstring 60 also disengages the proximal end 42 from hoop member 65 to facilitate removal of the pouch 40 through lumen 17 (See FIG. 2E). In this instance, hoop member 65 would remain within lumen 17 for subsequent removal after the endoscope is withdrawn from the operating site.

From the foregoing and with reference to the various figure drawings, those skilled in the art will appreciate that certain modifications can also be made to the present disclosure without departing from the scope of the same. For example and as mentioned above, it is contemplated that the proximal hoop member 65 and the pouch 40 may be selectively removable from one another to facilitate removal of the specimen. More particularly, pouch 40 may be configured such that controlled axial rotation of the hoop member 65 relative to the pouch 40 disengages the proximal end 42 of the pouch 40 from the hoop member 65 to allow the proximal end 42 of the bag to close about the specimen 100. Alternatively, the pouch 40 could be sutured to the hoop member 65 and the sutures withdrawn to disconnect the hoop member 65 from the pouch 40.

In a further embodiment, the retrieval apparatus is as discussed above with respect to FIGS. 1A–2E except that a tubular member is used in place of endoscope 12.

In an alternate embodiment, the grasping instrument 20 is integrated with the pouch 40 such that the grasping instrument 20 and the pouch 40 are removed simultaneously through the lumen 17. It is also contemplated that the hoop members 35 and 65 may be fabricated from bio-absorbable materials and configured to separate from the pouch 40 once cinched. Moreover, the support struts 28 may also be fabricated from a bio-absorbable material and removably connected to the hoop members 35 and 65.

Preferably, the longitudinally aligned struts 28 are biased to an arcuate shape and are positioned on or within the material of the pouch 40 to give the sides of the pouch 40 suitable structural integrity.

While certain embodiments of the disclosure has been described herein, it is not intended that the disclosure be limited thereto, as it is intended that the disclosure be as broad in scope as the art will allow and that the specification be read likewise. Therefore, the above description should not be construed as limiting, but merely as exemplifications of a preferred embodiment. Those skilled in the art will envision other modifications within the scope and spirit of the claims appended hereto.

What is claimed is:

1. An apparatus for withdrawing a tissue specimen, comprising:
    an endoscope including an endoscopic shaft having proximal and distal ends and a lumen extending therebetween;
    a first hoop-like support member selectively slideable within the lumen from a first position wherein the first hoop-like support member has a first diameter to at least one second position wherein the first hoop-like support member has a second diameter which is different from the first diameter;
    a pouch having first and second ends, the first end being an open end attached to the first hoop-like support member, the pouch defining a container therein for retaining the tissue specimen;
    a second hoop-like support member, the second end of the pouch being an open end attached to the second hoop-like support member; and
    a remote actuator disposed proximate the proximal end of the endoscopic shaft, the remote actuator being selectively actuateable to close the first end to encapsulate the tissue specimen.

2. An apparatus for withdrawing a tissue specimen according to claim 1 wherein the pouch includes at least one strut disposed between the hoop-like support members for further defining the container for retaining the tissue specimen.

3. An apparatus for withdrawing a tissue specimen according to claim 1 wherein the diameter of the second hoop-like support member is selectively expandable from a first diameter within the lumen to a second diameter outside the lumen.

4. An apparatus for withdrawing a tissue specimen according to claim 1 wherein the diameter of the first hoop-like support member is selectively contractible from a first diameter within the lumen to a second diameter within the lumen.

5. An apparatus for withdrawing a tissue specimen according to claim 1 wherein the first hoop-like support member includes a pair of arcuate portions which slidingly reciprocate with respect to one another to vary the diameter of the first hoop-like support member.

6. An apparatus for withdrawing a tissue specimen according to claim 1 wherein the first hoop-like support member is disposed in a pre-loaded configuration within the lumen such that the diameter of the first hoop-like support member automatically expands when the first hoop-like support member is extended from the distal end of the endoscopic shaft.

7. A method for withdrawing a tissue specimen through an endoscope comprising the steps of:
    providing:
    a grasping instrument;
    an endoscope including an endoscopic shaft having proximal and distal ends and a lumen extending therebetween;
    first and second hoop-like support members, each of the hoop-like support members being selectively slideable within the lumen from a first position to at least one second position, each of the hoop-like support members including a diameter which is variable from a first diameter to at least one different diameter; and
    a pouch having first and second ends which attach to respective first and second hoop-like support members, the pouch defining a container therein for retaining the tissue specimen;
    grasping the tissue specimen with the grasping instrument;
    sliding the first and second hoop-like members from the first to second positions such that the diameter of the second hoop-like member expands and encapsulates the tissue specimen;
    closing the second end of the pouch about the tissue specimen;
    withdrawing the grasping instrument through the lumen;
    closing the first end of the pouch about the tissue specimen; and
    withdrawing the tissue specimen and pouch proximally through the lumen.

8. An apparatus for retrieving a tissue specimen, comprising:
    a shaft having proximal and distal ends and a lumen extending therebetween;
    a first support member in the shape of a loop and a second support member in the shape of a loop, the first support member and the second support member being slidably received in the lumen; and
    a pouch extending between the first support member and the second support member, the second support member being expandable form a first configuration to a second configuration.

9. An apparatus for withdrawing a tissue specimen, comprising:

an endoscope including an endoscopic shaft having proximal and distal ends and a lumen extending therebetween;

at least one hoop-like support member selectively slideable within the lumen from a first position wherein the hoop-like support member has a first diameter to at least one second position wherein the hoop-like support member has a second diameter which is different from the first diameter, the hoop-like support member including a pair of arcuate portions which slidingly reciprocate with respect to one another to vary the diameter of the hoop-like support member;

a pouch having first and second ends, the first end being an open end attached to the hoop-like support member, the pouch defining a container therein for retaining the tissue specimen; and a remote actuator disposed proximate the proximal end of the endoscopic shaft, the remote actuator being selectively actuateable to close the first end to encapsulate the tissue specimen.

\* \* \* \* \*